United States Patent
Tyler

[11] Patent Number: 5,596,414
[45] Date of Patent: *Jan. 21, 1997

[54] SOLID STATE SPECTROFLOURIMETER AND METHOD OF USING THE SAME

[76] Inventor: Jonathan M. Tyler, 8306 Davies Road, Edmonton, Alberta, Canada, T6E 4Y5

[*] Notice: The term of this patent shall not extend beyond the expiration date of Pat. No. 5,422,726.

[21] Appl. No.: 461,552

[22] Filed: Jun. 5, 1995

Related U.S. Application Data

[63] Continuation of Ser. No. 25,362, Feb. 16, 1993, Pat. No. 5,422,726.

[51] Int. Cl.⁶ .................................................. G01N 21/64
[52] U.S. Cl. ...................... 356/417; 356/317; 250/458.1
[58] Field of Search ....................................... 356/317, 318, 356/417, 244; 250/458.1, 459.1, 461.1, 461.2

[56] References Cited

U.S. PATENT DOCUMENTS

| | | | |
|---|---|---|---|
| 3,810,696 | 5/1974 | Hutchins, Jr. . | |
| 3,975,098 | 8/1976 | West . | |
| 4,076,421 | 2/1978 | Kishner | 356/236 |
| 4,181,442 | 1/1980 | Niemann et al. | 250/461.1 |
| 4,241,998 | 12/1980 | Farkas et al. | 356/319 |
| 4,276,780 | 7/1981 | Patel et al. | 73/643 |
| 4,279,506 | 7/1981 | Maines | 250/458.1 |
| 4,293,225 | 10/1981 | Wheaton et al. | 356/417 |
| 4,295,199 | 10/1981 | Curry et al. | 250/461.2 |
| 4,301,372 | 11/1981 | Giering et al. | 356/317 |
| 4,303,343 | 12/1981 | Patel et al. | 356/432 |
| 4,310,249 | 1/1982 | Kramer | 356/414 |
| 4,395,126 | 7/1983 | Kramer | 356/417 |
| 4,531,834 | 7/1985 | Nogami | 356/318 |
| 4,537,861 | 8/1985 | Elings et al. | 356/317 |
| 4,553,034 | 11/1985 | Byers et al. | 250/458.1 |
| 4,558,014 | 12/1985 | Hirschfeld et al. | 356/445 |
| 4,650,336 | 3/1987 | Moll | 356/417 |
| 4,753,530 | 6/1988 | Knight et al. | 356/73 |
| 4,832,555 | 5/1989 | Ohnishi . | |
| 4,895,445 | 1/1990 | Granger | 356/328 |
| 4,919,535 | 4/1990 | Hohberg et al. | 356/429 |
| 4,921,351 | 5/1990 | Kohigashi et al. | 356/323 |
| 4,921,788 | 5/1990 | Deustch | 435/6 |
| 4,962,045 | 10/1990 | Picozza et al. | 356/501 |
| 5,014,216 | 5/1991 | Stafford et al. | 364/496 |
| 5,422,726 | 6/1995 | Tyler | 356/417 |

FOREIGN PATENT DOCUMENTS

| | | | |
|---|---|---|---|
| 0252578A2 | 1/1988 | European Pat. Off. . | |
| 198849 | 12/1982 | Japan | 356/417 |
| WO89/07757 | 8/1989 | WIPO | 250/458.01 |
| WO9323738 | 11/1993 | WIPO . | |

Primary Examiner—F. L. Evans
Attorney, Agent, or Firm—Cushman Darby & Cushman IP Group of Pillsbury Madison & Sutro LLP

[57] ABSTRACT

The spectrofluorimeter according to the present invention advantageously uses a triggered xenon flash tube powered with a capacitor store and controlled by program instructions from a microcontroller. Also included is an optical cell having a configuration in which the xenon flash tube is placed in spaced relation to a pair of signal detectors and a reference detector. The spaced relation of these components substantially helps allow the use of solid detectors in the spectrofluorimeter. Electrical isolation of the detector amplifiers during all periods except for the actual detection portion of the flash cycle is obtained to enhance the noise immunity of the spectrofluorimeter detection system.

30 Claims, 14 Drawing Sheets

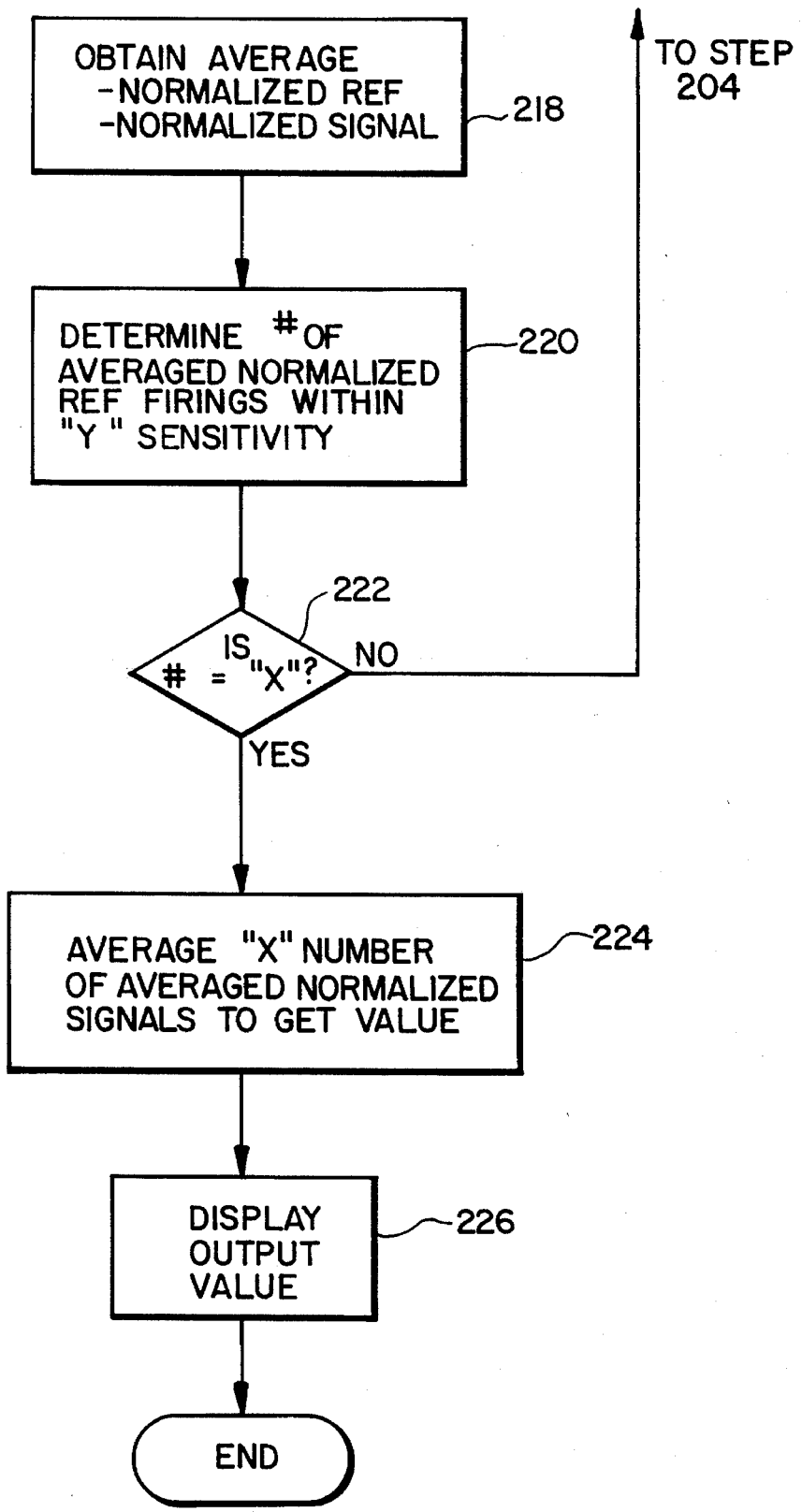

FIG. 17

| TYLER RESEARCH CONCENTRATION | TYLER RESEARCH CELL COUNTING | TYLER RESEARCH FLUORESCENCE |
|---|---|---|
| ALIQUOT VOLUME IN CUVETTE 10ul | PG DNA CELL? 14pg | INSERT UNKNOWN PRESS ENTER |
| INSERT 0 ug/ml STD PRESS ENTER | INSERT 0 ug/ml STD PRESS ENTER | Raw: 846 |
| INSERT 50 ug/ml STD PRESS ENTER | INSERT 50 ug/ml STD PRESS ENTER | |
| INSERT UNKNOWN PRESS ENTER | INSERT UNKNOWN PRESS ENTER | |
| 846 = 499 ng Orig: 50.0 ug/ml | 845 = 500ng DNA 71371 CELLS | |

SOLID STATE SPECTROFLOURIMETER AND METHOD OF USING THE SAME

This is a continuation of Application 08/025,362, filed Feb. 16, 1993, now U.S. Pat. No. 5,422,726.

BACKGROUND OF THE INVENTION

1. The Field of the Art

The present invention relates to a spectrofluorimeter.

2. Description of the Related Art

Spectrofluorimeters are used to detect the presence of certain molecular structures in a specimen. Specifically, in the presence of a solution containing a fluorophore, certain molecular structures are known to interact with the fluorophore such that the incident light of a particular wavelength is absorbed and light having a different wavelength is emitted. Measuring the light emitted at the fluorophore wavelength, due to the presence of the molecular structure of interest in the specimen, allows for the determination of the quantity of the molecular structure of interest in the specimen.

For example, ethidium bromide (EtBr) is used a fluorophore to detect the presence of nucleic acids by virtue of its intercalation into the nucleic acid chain. Monochromatic light having a wavelength of 520 nanometers is irradiated on the solution containing the specimen of interest. By measuring the quantity of light emitted at a wavelength of 600 nanometers allows the concentration of the nucleic acid in the specimen to be determined.

While spectrofluorimetry has been known many years, spectrofluorimeters are typically very large in size, delicate and exceptionally expensive. Many reasons for this exist.

One such reason is that spectrofluorimeters typically require a very large, steady state light source. Such a light source generates large quantities of heat, which requires the distance of the light source from the specimen to be quite large. Furthermore, these light sources typically require mechanical choppers and complicated light directing mechanisms. For example, reference is made to U.S. Pat. Nos. 3,832,555 and 4,531,834.

Furthermore, in order to have wide commercial applications, the detectors of the spectrofluorimeter must be adaptable for use with widely available fluorophore dyes. Furthermore, electrical noise generated by the light source is high in spectroflourimeters generally. These factors have inhibited the use of solid state detectors being used in spectrflourimeters. In the past, Hofer Scientific offered a solid state detector spectrofluorimeter, but this spectroflorimeter could only measure Hoechst dyes due to the requirement that it detect in infrared wavelengths. Thus, this spectroflourimeter could not be used to detect wavelengths in the visible spectrum. Also, the specimen itself was destroyed when using the Hoechst dyes.

SUMMARY OF THE INVENTION

It is an object of the present invention to provide a solid state spectrofluorimeter having high immunity from undesired noise.

It is another object of the present invention to provide a solid state spectrofluorimeter that uses a triggered light source.

Another object of the spectrofluorimeter according to the present invention is to provide a solid state spectrofluorimeter that requires a low power light source.

It is a further object of the present invention to provide a solid state spectrofluorimeter capable of detecting light in the visible spectrum using commercially available fluorophores.

Still a further object of the present invention to provide a spectrofluorimeter of compact size and which is easy to use.

In order to attain the above recited objects of the invention, among others, the present invention advantageously uses a triggered xenon flash tube. Powered with a capacitor store, the xenon flash tube is connected in parallel with a matched resistive load, which resistive load increases the lifespan of the xenon flash tube as well as increases the duration of the light pulse itself Furthermore, spectrofluorimeter according to the present invention uses an optical cell having a configuration in which the xenon flash tube is placed in spaced relation to a pair of signal detectors and a reference detector. The spaced relation of these components substantially helps allow the use of solid state detectors in the spectroflourimeter.

The spectroflourimeter according to the present invention also provides electrical isolation of the detector amplifiers during all periods except for the actual detection portion flash cycle. This helps enhance the noise immunity of the spectroflourimeter detection system.

Also, the solid state spectrofluorimeter according to the present invention advantageously uses a microcontroller to control the flash timing of the xenon flash tube and the timing of electrical isolation of the detector amplifier circuits.

Thus, the solid state spectrofluorimeter described above advantageously allows the detection of molecular structures in a specimen using a commonly available fluorophores detectable in the visible spectrum.

BRIEF DESCRIPTION OF THE DRAWINGS

These and other advantages of the present invention may be appreciated from studying the following detailed description of the preferred embodiment together with the drawings in which:

FIG. 17 illustrates various display options available to the user using the spectrofluorimeter according to the present invention.

DETAILED DESCRIPTION OF THE PREFERRED EMBODIMENT

Figure 1:
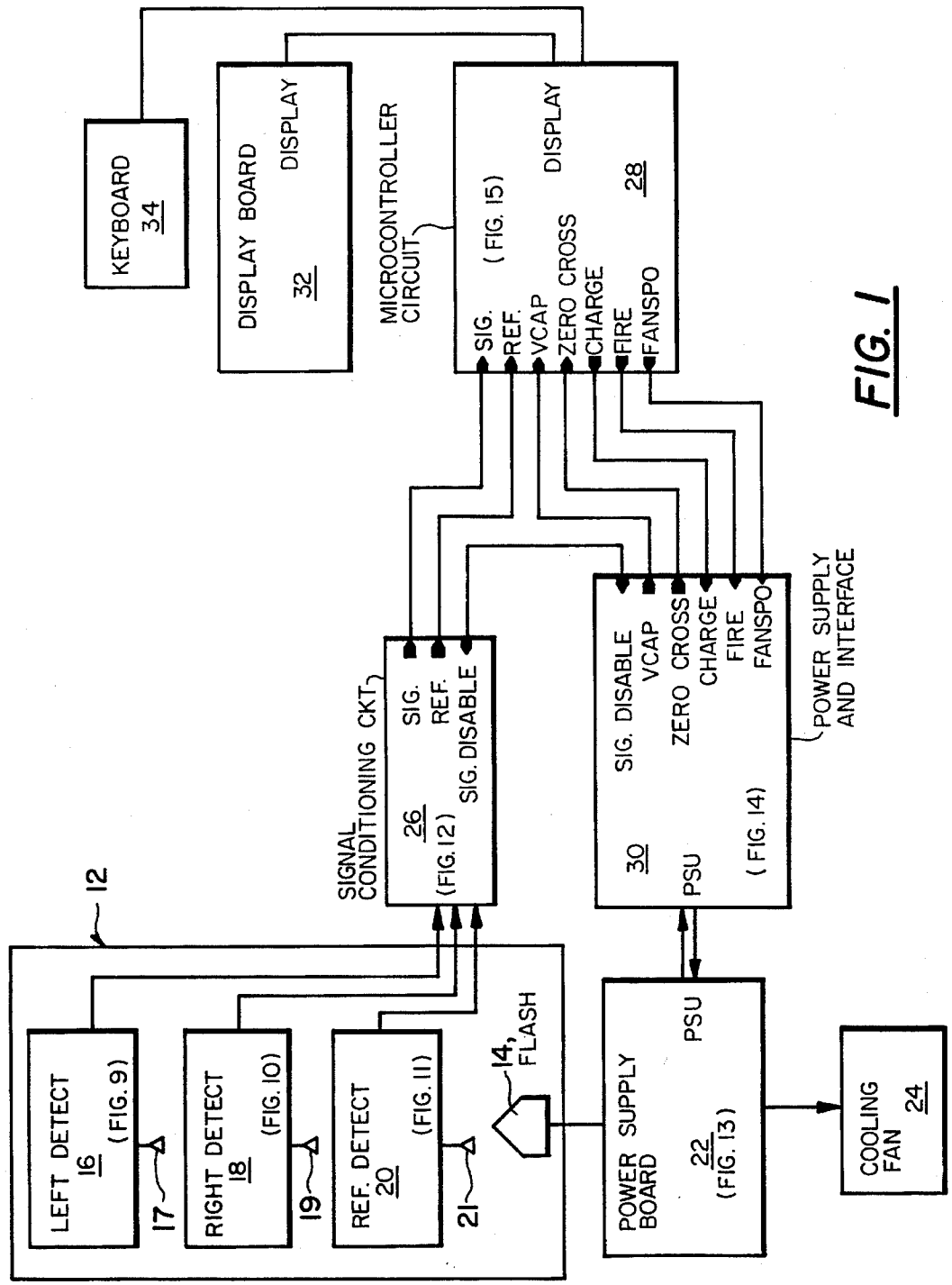
FIG. 1 illustrates a block diagram of the spectrofluorimeter according to the present invention.

FIG. 1 illustrates a block diagram of the spectrofluorimeter 10 according to the present invention. Major components of the spectrofluorimeter 10 include the optical cell 12, which includes a xenon flash 14, a left signal detector circuit 16, a left signal detector 17, a right signal detector circuit 18, a right signal detector 19, a reference detector circuit 20 and a reference signal detector 21. The xenon flash tube is powered by charge stored in a storage capacitor located in the power supply circuit 22, which circuit also supplies power to operate a cooling fan 24.

Signal conditioning circuit 26 received the detected signals from the left signal detector circuit 16, the right signal detector circuit 18, and the reference detector circuit 20. Signal conditioning circuit 26 amplifies, shapes and sums the detected signals, as well as detected reference signals, and transmits the same to the microcontroller circuit 28. Interface circuit 30 transmits signals between power supply circuit 22 and microcontroller circuit 28 and signal conditioning circuit 26 as described hereinafter.

The analysis results obtained from operation of the spectrofluorimeter 10 are displayed on display 32, which can be an LED display of numerical values or a monitor which provides a graphical display. Keyboard 34 allows entry of the mode of operation, initial conditions, and various sensitivity characteristics described hereinafter. Either discreet function keys or multi-function up/down keys which allow various entries using the same up/down key pressed repeatedly and are software programmed can be used.

Figure 2:
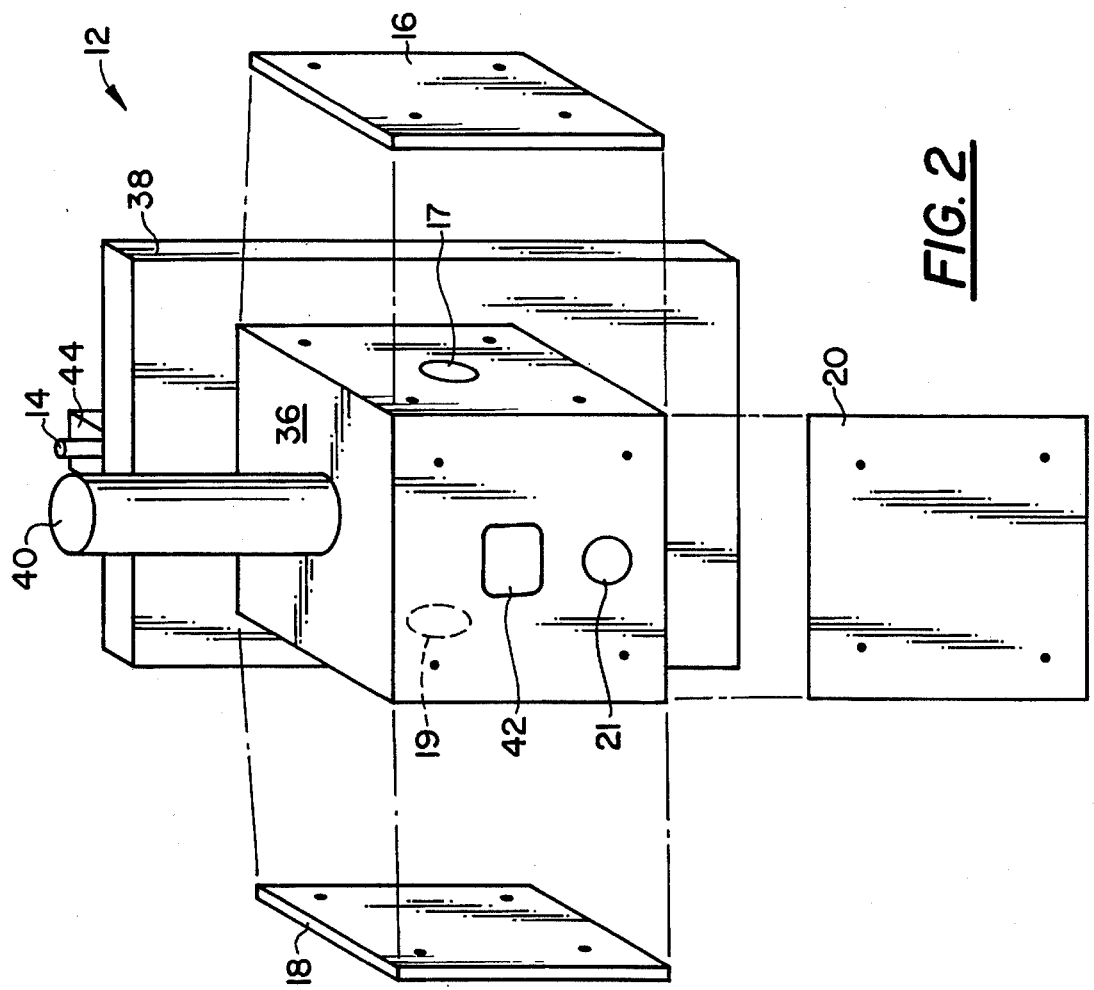
FIG. 2 illustrates a perspective view of the optical cell according to the present invention.

FIG. 2 illustrates optical cell 12. The optical cell 12 contains a machine tooled cell cavity 36 which is preferably made of a black phenolic resin or a flat black anodized aluminum. Cell cavity 36 is approximately 4 cm³ in outer dimensions and is mounted on an anodized black aluminum plate 38 which shields the xenon flash tube from the cell cavity 36, except as described hereinafter. Cell cavity 36 is also provided with an opening that allows the insertion of a cuvette 40, which will contain the specimen of interest in the fluorophore solution. Cell cavity 36 also contains openings for the left signal detector 17, the right signal detector 19, reference signal detector 21 and light absorbing medium 42.

Flash holder 44 supports xenon flash 14 in place and is made of Corian, an acrylic/aluminum hydroxide compound.

Each of the detectors 17, 19 and 21 disposed in the optical cell 12 are electrically connected to the left signal detector circuit 16, the right signal detector circuit 18, and the reference detector circuit 20, respectively. Each of detector circuits 16, 18 and 20 are mounted directly over the detectors disposed in the optical cell 12. This placement minimizes the electrical path length the detected signals must travel before initial amplification, as described hereinafter.

Figure 3:
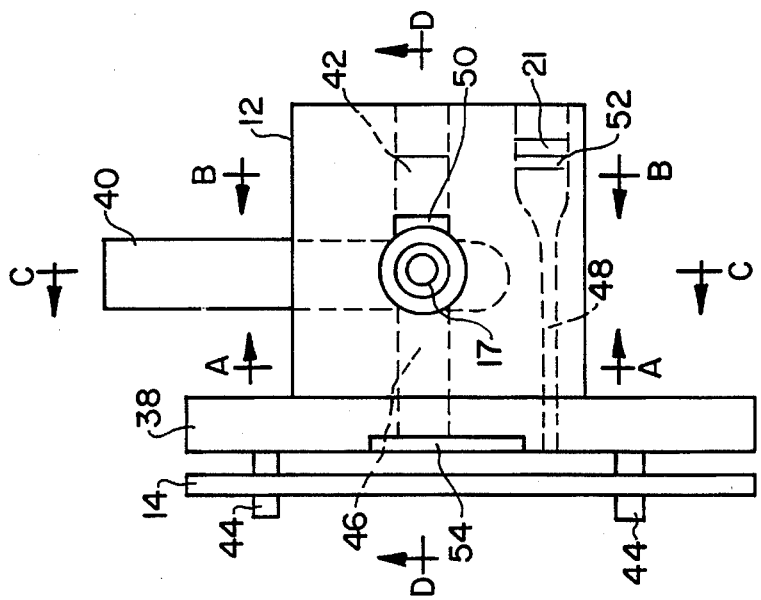
FIG. 3 illustrates a left side view of the optical cell according to the present invention.

FIGS. 3–8 illustrate the various cross sectional views of the optical cell.12. As seen in FIG. 3, the dashed lines illustrate openings formed in the optical cell 12 for insertion of the detectors 17, 19 and 21, as well as the. cuvette 40. Furthermore, light pathways are provided by these openings for the required optical transmission paths.

Figure 5A:
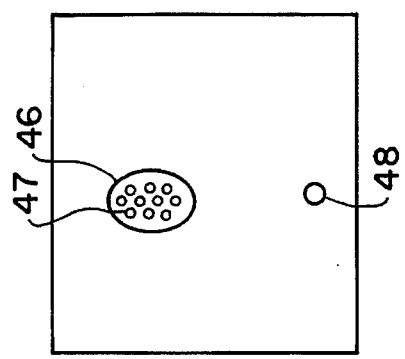
FIG. 5A illustrates a cross section for another embodiment of a portion of the optical cell illustrated in FIG. 5.
Figure 5:
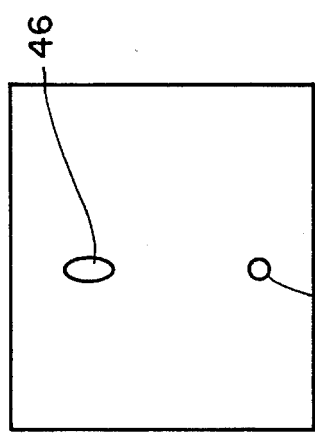
FIG. 5 illustrates a cross section view taken along line A—A the optical cell illustrated in FIG. 3.

As seen more clearly in FIG. 5, which is the A—A cross section of FIG. 3, the opening between the xenon flash 14 and the cuvette 40 is a rectangular slit 46 having a width of 3 mm and a height of 7 mm.

An alternative to rectangular slit 46 is a plurality of approximately ten holes 47 having a diameter of about 0.7 mm arranged in a pattern as a rectangular slit 46, as illustrated in FIG. 5A. Though more difficult to machine such a pattern of holes 47, this pattern can better focus the light radiating from the xenon flash 14 to the specimen within cuvette 40.

The distance between the xenon flash 14 and the cuvette is 10 mm. Provided in the optical pathway is interference filter 54, disposed between the xenon flash 14 and the cuvette 40.

An opening 48 is provided to allow the direct transmission of light generated from the xenon flash 14 to the reference detector 21. Opening 48 has a diameter of 0.35 mm and for approximately three quarters of the 35 mm distance between the xenon flash 14 and the reference detector 20 maintains this diameter. The small diameter of opening 48 relative to opening 46 helps diminish the amount of light transmitted from xenon flash 14 onto detector 21. This helps equalize the amount of light which actually reaches each of the detectors 17, 19 and 21.

Figure 6:
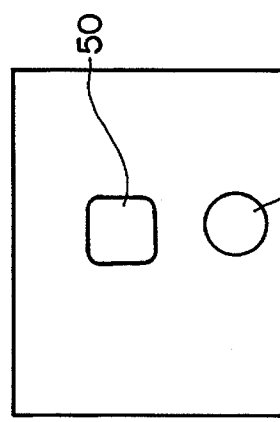
FIG. 6 illustrates a cross section view taken along line B—B of the cell illustrated in FIG. 3.
Figure 4:
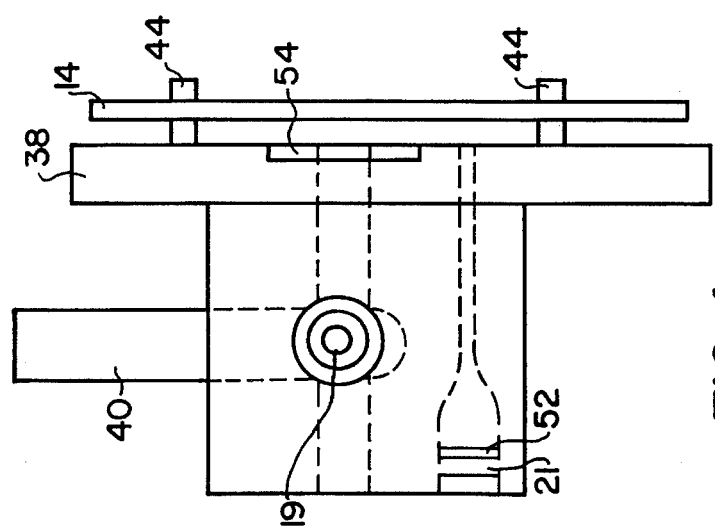
FIG. 4 illustrates a right side view of the optical cell according to the present invention.

FIG. 6 illustrates more clearly the light absorbing medium 42 disposed directly behind the cuvette 40. This helps ensure that light from the xenon flash tube that passes through cuvette 40 is not reflected and, subsequently, detected by detectors 17 and 19. This helps ensure that only florescent light is detected by detectors 17 and 19. FIG. 6 also illustrates the larger diameter of opening 48 in the vicinity of reference detector 21, which is needed in order to properly position the reference detector 21. FIG. 6 also illustrates that neutral density reference filter 52 is placed between xenon flash 14 and detector 21, directly in front of detector 21. This further helps equalize the amount of light which actually reaches each of the detectors 17, 19 and 21.

Figure 7:
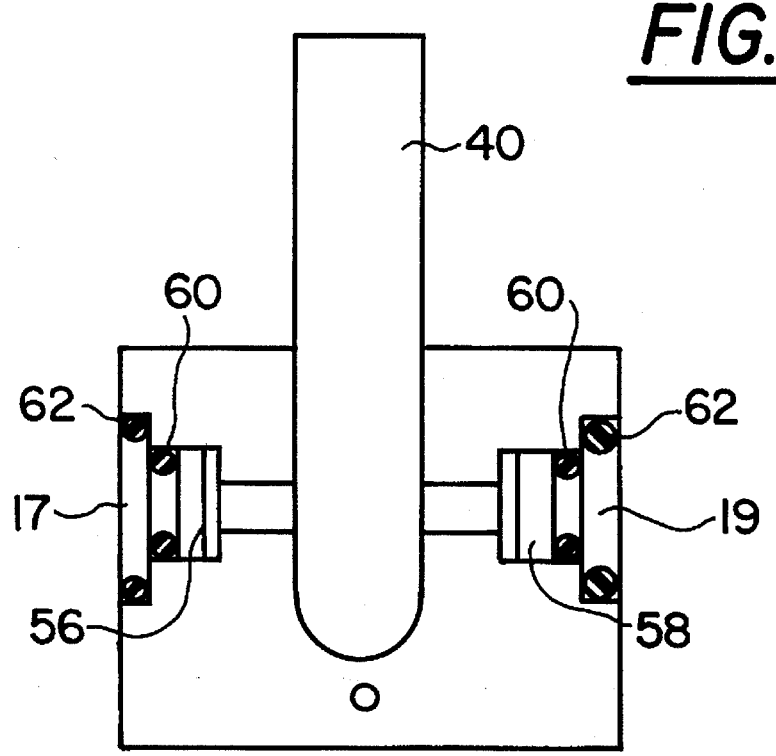
FIG. 7 illustrates a cross section view taken along line C—C of the cell illustrated in FIG. 3.
Figure 8:
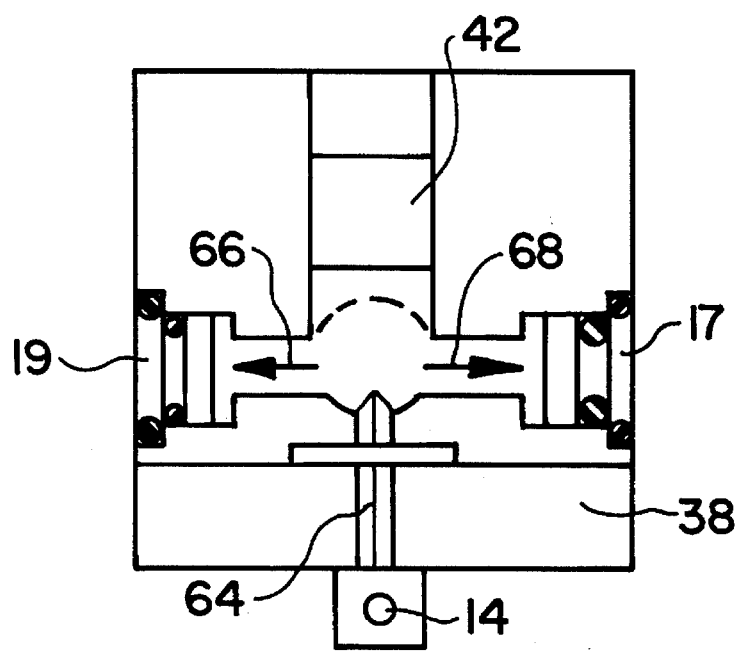
FIG. 8 illustrates a cross section view taken along line D—D of the cell illustrated in FIG. 3.

FIGS. 7 and 8 are helpful in describing the optical characteristics of the optical cell 12. Referring to FIG. 7, it can be seen that the cuvette 40, which contains the specimen to be analyzed in solution, and is disposed midway between each of detectors 17 and 19. Cuvette 40 preferably has an outer diameter of about 10 mm, although a different size or shaped cuvette 40 can, of course, be used. The preferred distance between the out diameter of the cheviot and each of detector 17 and 19 is 10 mm.

Disposed in front of each of detectors 17 and 19 are high bandpass emission filters 56 and 58. These filters eliminate wavelengths below the wavelength of interest. If ethidium bromide (EtBr) is used as the fluorophore, each filter 56 is preferably an OR570 filter that allows light over 590 nm to pass while blocking virtually all light having a wavelength below 550 nm. Each of high bandpass emission filters 56 and 58 are held in light tight configuration by O-rings 60 and 62. Each pair of O-rings 60 and 62 are compressed upon insertion of the detectors 17 and 19 into the optical cell 12.

FIG. 8 illustrates the path 64 that light from the xenon flash 14 travels to properly strike the specimen solution contained in cuvette 40. Paths 66 and 68 illustrate the path of the florescent light detected by detectors 17 and 19, respectively, which paths are preferably at 90° to path 64.

Figure 9:
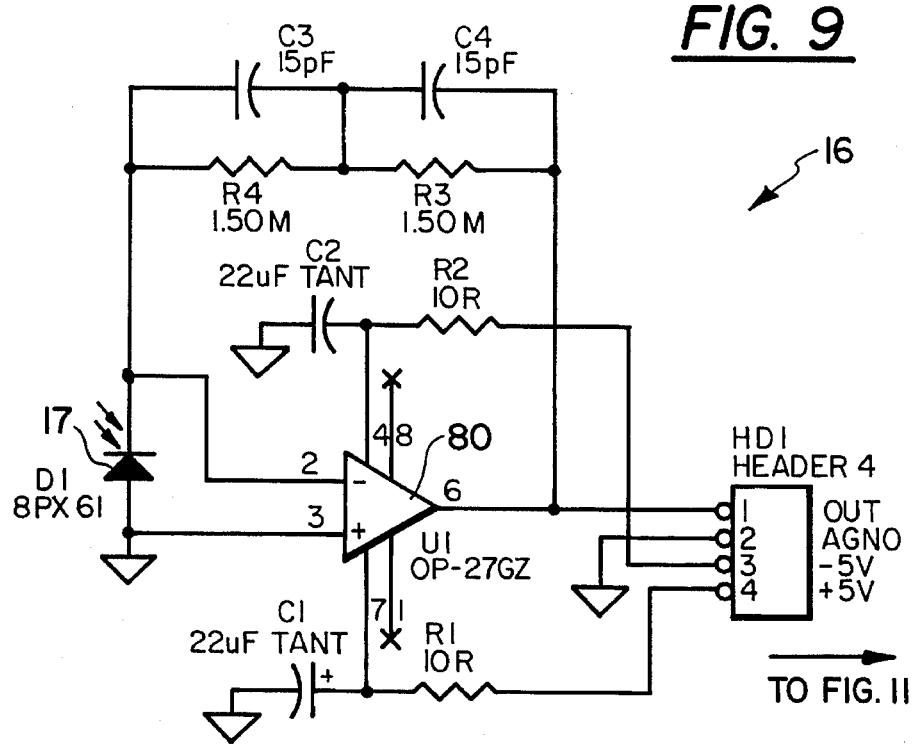
FIG. 9 illustrates the initial amplification circuitry used with the left signal detector of the spectrofluorimeter according to the present invention.

FIG. 9 illustrates the left signal detector circuit 16 represented in block diagram form in FIG. 1 and as a circuit board in FIG. 2. The detector 17 is preferably a Siemen's BPX 61 photodiode and, because it is an extremely sensitive photodiode, is used with no bias voltage. Operational amplifier 80 provides initial amplification of the signal detected by detector 17. The various capacitors and resistors illustrated in FIG. 9 provide proper biasing and wave shaping.

Figure 10:
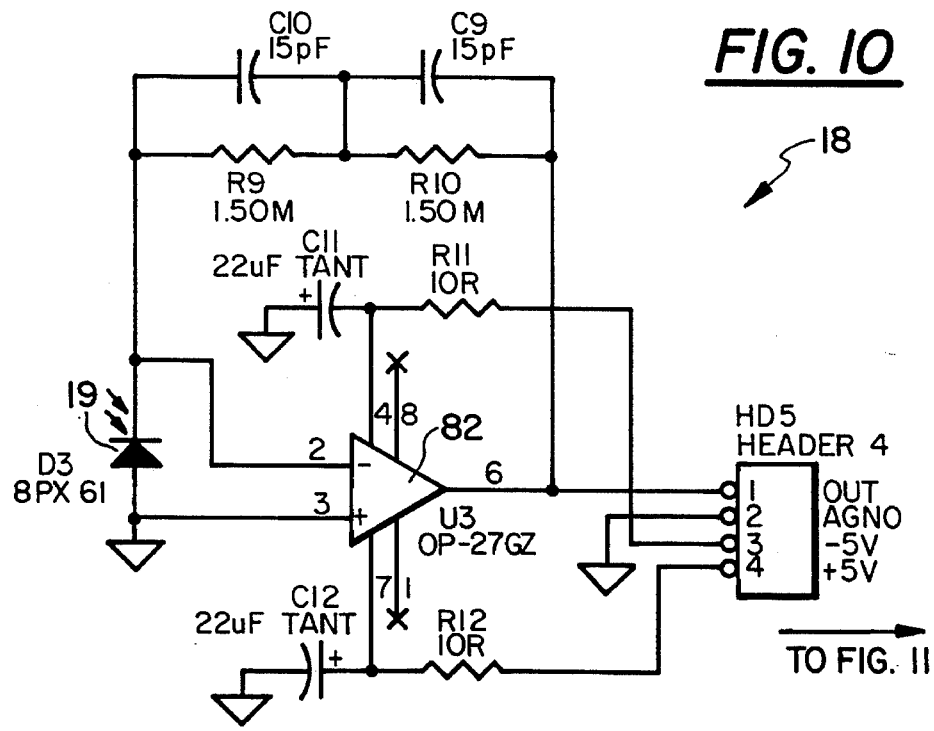
FIG. 10 illustrates the initial amplification circuitry used with the right signal detector of the spectrofluorimeter according to the present invention.

FIG. 10 illustrates the right signal detector circuit which is identical to a left sensor board 16 previously described with referenced to FIG. 9. Detector 18 is again a Siemen's BPX 61 photodiode and is also used with no bias voltage. Care should be taken to obtain detectors 17 and 19 that have matched electrical characteristics.

Figure 11:
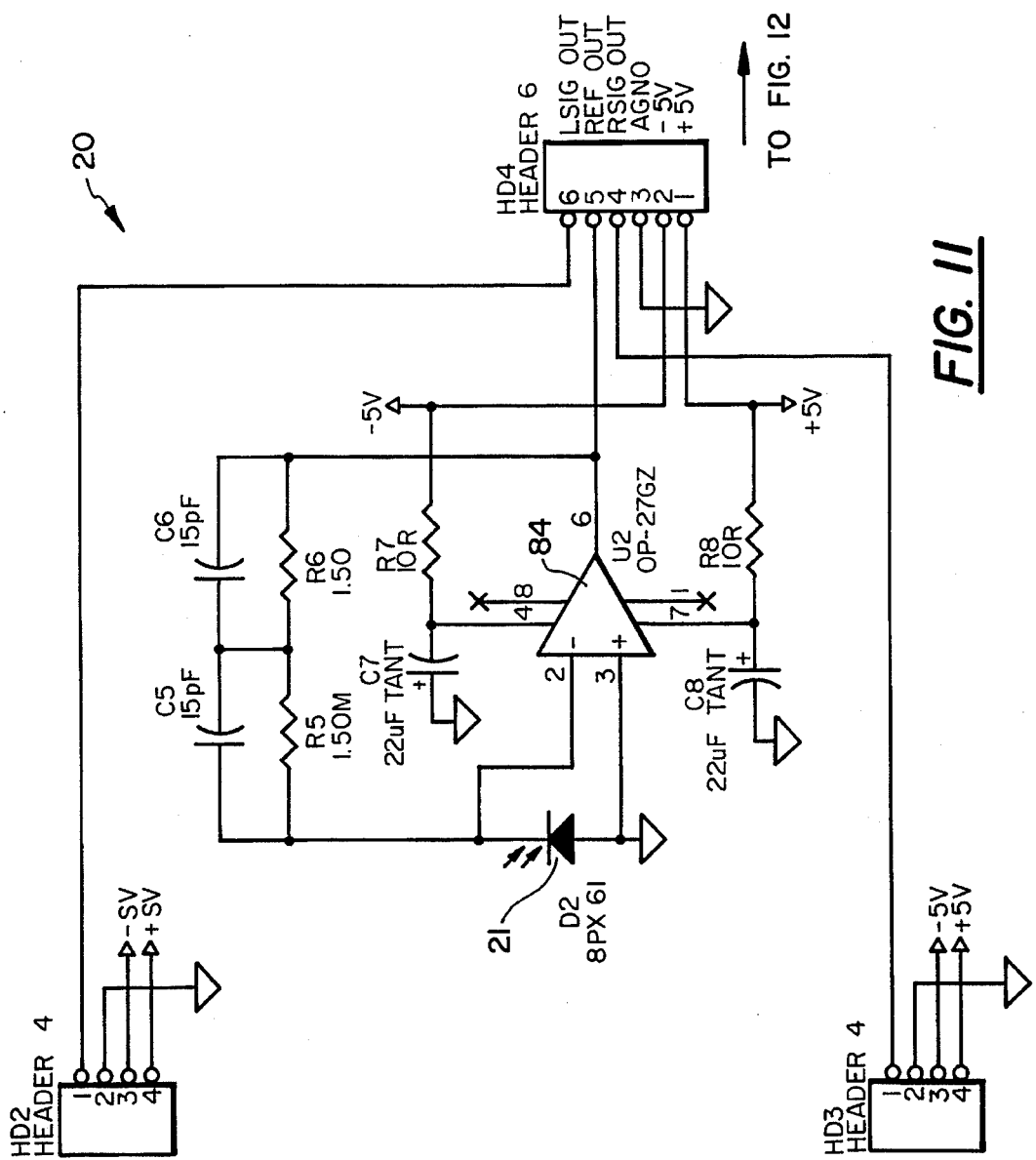
FIG. 11 illustrates the initial amplification circuitry used with the reference signal detector of the spectrofluorimeter according to the present invention.

FIG. 11 illustrates the reference detector circuit 20 which also uses a Siemen's BPX 61 photodiode as detector 21 and which is also used with no bias voltage. The detected signal is amplified by operational amplifier 84. The wave shaping and noise reducing circuitry associated with operational amplifier 84 is identical to circuitry used with the detectors 17 and 19 in order to obtain maximum performance.

Figure 12:
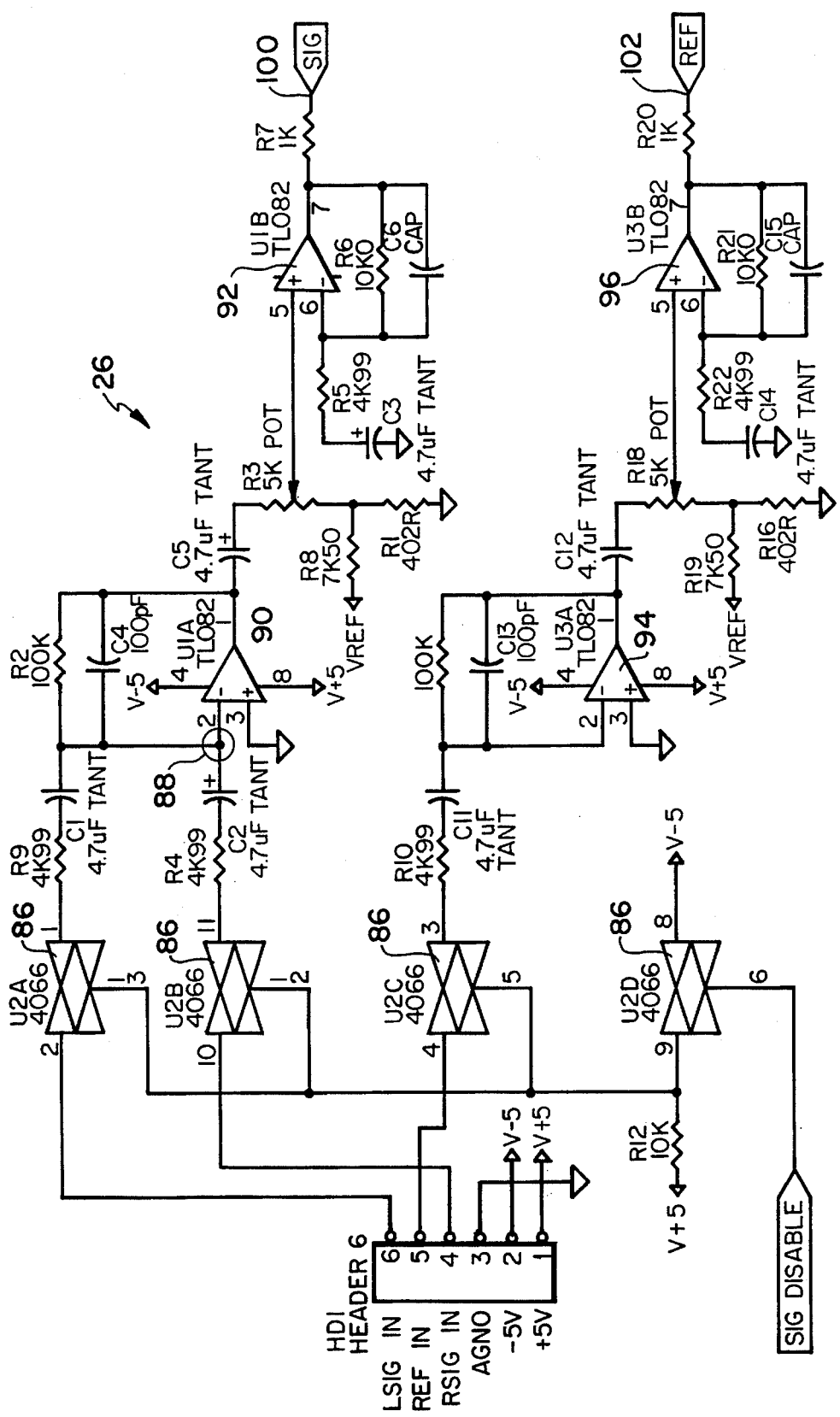
FIG. 12 illustrates the signal conditioning circuitry of the spectrofluorimeter according to the present invention.

FIG. 11 also, illustrates that the once amplified detected signals from detectors 17 and 19, respectively, as well as the once amplified signal from detector 21 are all output to the signal conditioning circuit 26, illustrated in FIG. 12.

Each of the detected signals pass through triggered switch 86 during a period of time determined by the DISABLE signal, described hereinafter. The detected and once amplified signals from the left signal detector 16 and the right signal detector 18 are summed at node 88 and then twice amplified by operational amplifiers 90 and 92. Again, the associated resistors and capacitors help with establishing noise immunity and proper waveshaping.

The reference detector signal is likewise twice amplified by operational amplifiers 94 and 96. Identical noise reducing and wave shaping circuitry is associated with operational amplifiers 94 and 96. The detected signal 100 output from operational amplifier 92 and the reference signal 102 output from the operational amplifier 96 are each input to the microcontroller circuit 28 illustrated in FIG. 15 as described hereinafter.

Figure 13A:
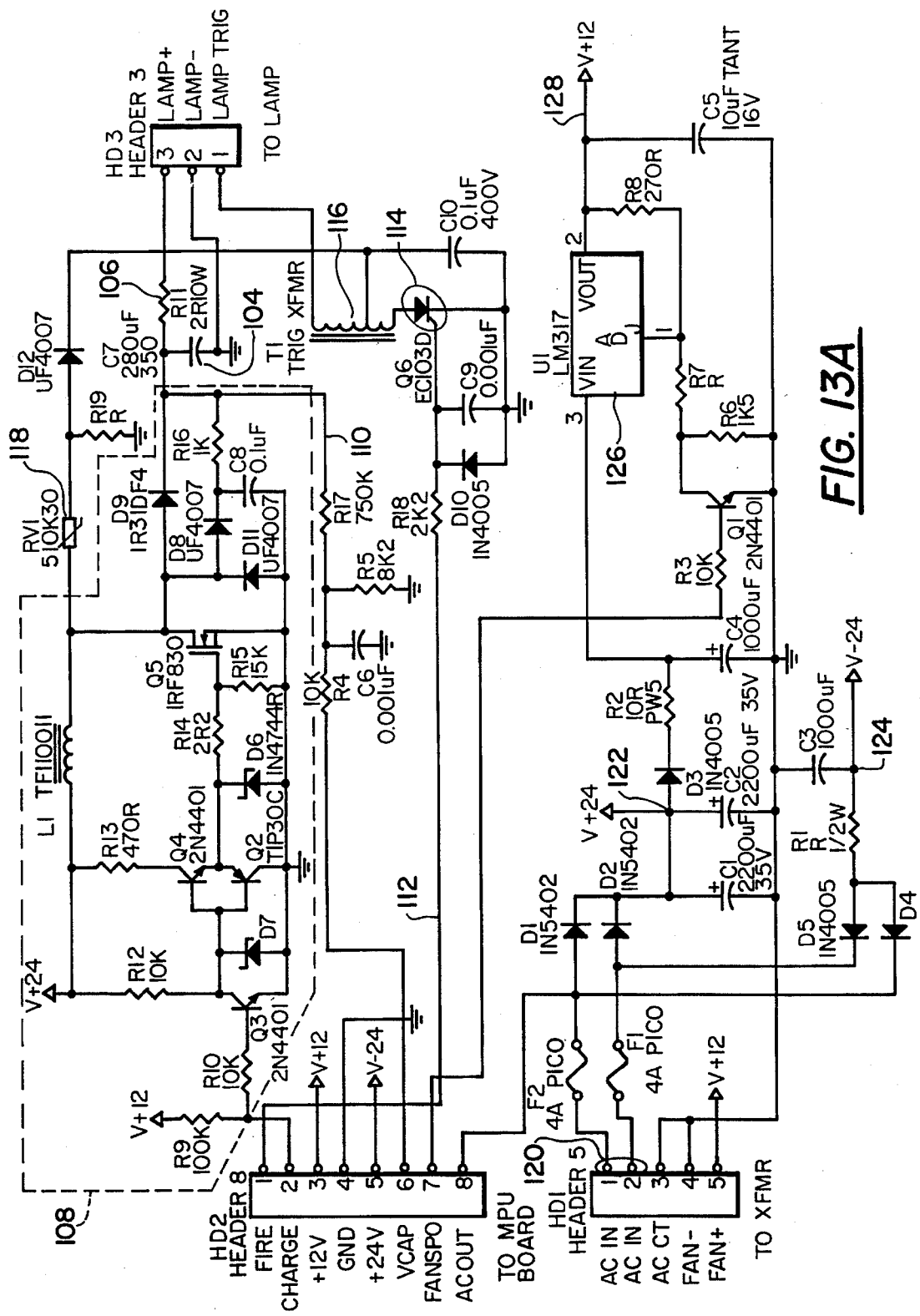
FIG. 13 illustrates the power supply circuitry used in the spectrofluorimeter according to the present invention.

FIG. 13 illustrates the power supply 22 used to power the xenon flash 14 and the cooling fan 24 illustrated in FIG. 1. Power supply 22 powers the xenon flash 14 using charge stored in capacitor 104. Resistor 106 is used to extend the duration of the xenon flash tube pulse and also extends the lifetime of the xenon flash tube by reducing the voltage across the terminals of the xenon flash itself. In operation, capacitor 104 is triggered at 240 volts due to the presence of resistor 106 and a 600 nm pulse of 30,000 watts is obtained, when integrated over the duration of the pulse.

The CHARGE signal, input to the capacitor charging circuit 108, initiates charging of capacitor 104. Of note, a matched set of zener diodes having a 15 volt nominal zener voltage are used to stabilize the charging of the capacitor 104.

Capacitor 104, when fully charged, develops a VCAP signal on line 110, which signal is then input into microcontroller circuit 28 and used as hereinafter described.

When capacitor 104 is fully charged, the xenon flash 14 is ready for firing. Upon receipt transmission of a FIRE signal along line 112, silicon controlled rectifier 114 begins conducting. This causes transmitter transformer 116 to turn on the xenon flash 14. Thus, charge stored in capacitor 104 powers the xenon flash 14, which thereby illuminates the specimen solution in cuvette 40 and the reference detector 21, illustrated in FIG. 2.

Also illustrated in FIG. 13 is an overvoltage protection device, specifically varistor 118, which will eliminate surges in the voltage used to charge the capacitor 104.

Power supply circuit 22 obtains it DC power using a stepped power supply configuration. AC power input from line 120 develops a positive 24 DC volts at node 122 and a negative 24 DC volts at node 124 using diodes and smoothing capacitors. A positive 12 DC volts is obtained using a three terminal positive voltage regulator 26 such that a positive 12 DC volts result on line 128. This positive 12 DC volts is then input into two different three terminal low current 5 volt positive DC regulators 130 and 132 to obtain VCC DC voltage and positive 5 DC volts. Similarly, the negative 24 volts from line 124 is input into a three terminal low current 5 volt negative DC regulator 134 in order to obtain negative 5 DC volts.

Figures 13B, 14:
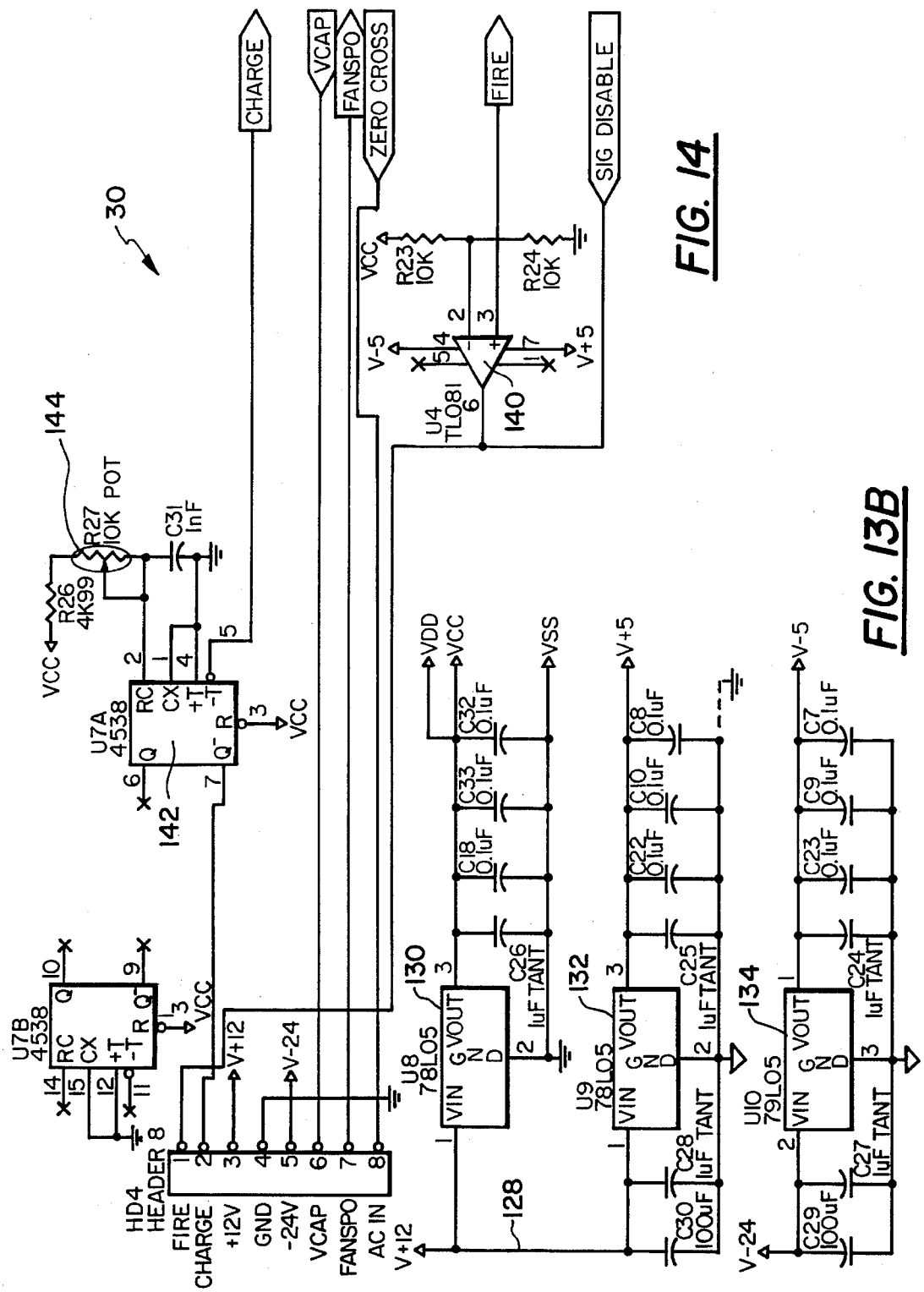
FIG. 14 illustrates the interface circuitry used by the spectrofluorimeter according to the present invention.
Figure 15:
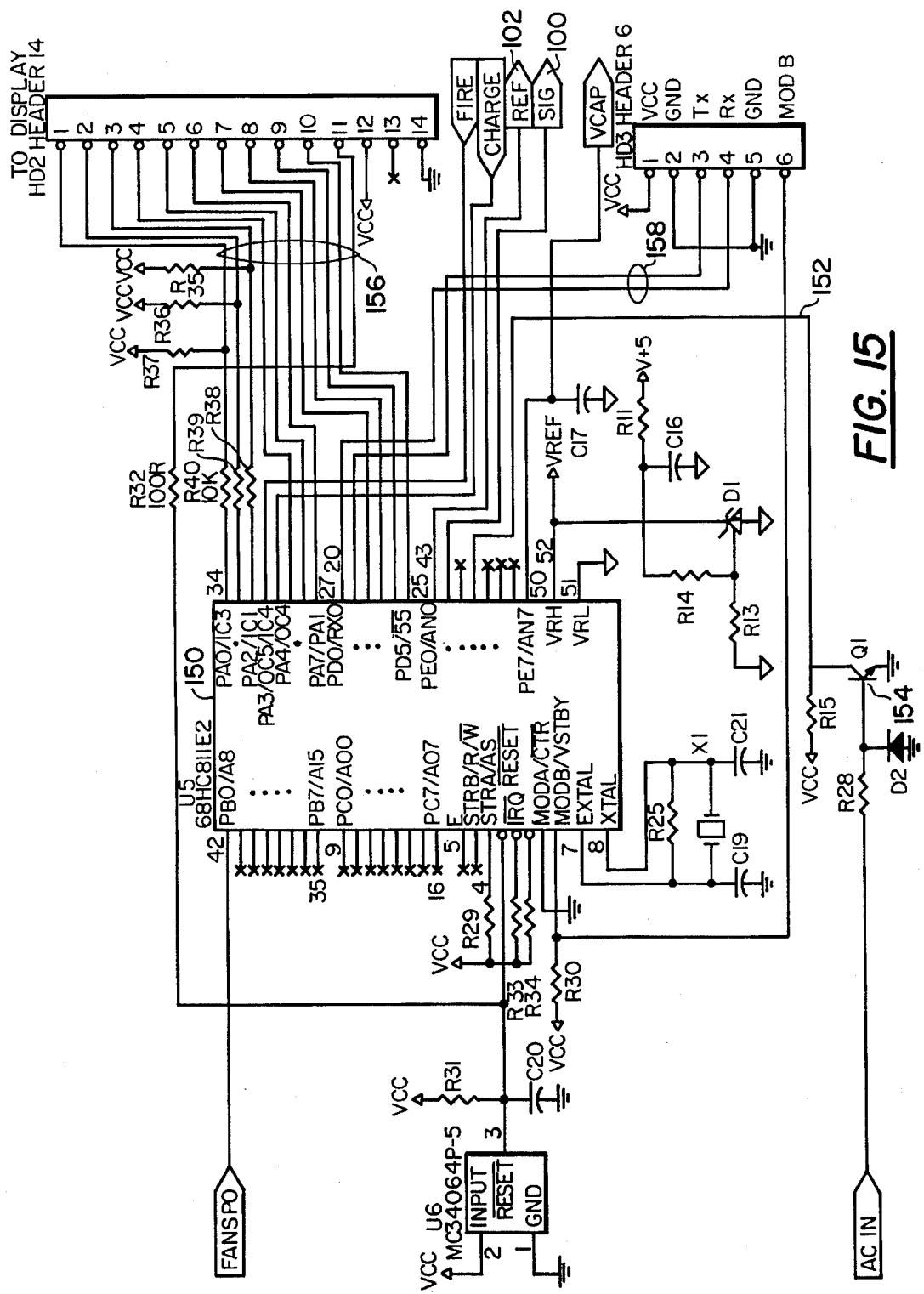
FIG. 15 illustrates the microcontroller circuitry used with the spectrofluorimeter according to the present invention.

FIG. 14 illustrates the interface circuit 30 between the power supply circuit 22 illustrated in FIG. 13 and microcontroller circuit 28 illustrated in FIG. 15. VCAP and the AC signal are passed directly from the power supply circuit 22 to the microcontroller circuit 28. However, the FIRE signal received from microcontroller circuit 28 is first amplified using up amp 140. The FIRE signal is then supplied to the power supply circuit 22 to fire the xenon flash 14 as described previously. The CHARGE signal is input from the microcontroller circuit 28 to a flipflop 142. Flipflop 142 maintains at its output a signal corresponding in level according to the CHARGE signal until microcontroller circuit 28 develops another CHARGE signal in response to an input of the VCAP signal previously described. This ensure that capacitor 104 of FIG. 113 is fully charged prior to firing of xenon flash 14.

As also illustrated in FIG. 14, the FIRE signal, as amplified by operational amplifier 140, is then also used as the DISABLE signal input to signal conditioning circuit 26. The DISABLE signal, as described previously, effectively connects the detectors 17, 19 and 21 to the signal conditioning circuit 26, as switches 86 of FIG. 12 are in a normally open position. This protects the optical detector 17, 19 and 21 and associated amplification circuits 16, 18, 20 and 26 during capacitor charging and at the onset of flash ignition.

Xenon flash 14 delivers approximately 30,000 watts when integrated over the duration of the pulse used to obtain detector samples. Although the xenon pulse contains a number of distinct peaks and valleys, the xenon emission spectrum is broad based with ample output in the visible light range. By thus triggering the capacitor 104 and using the matched resistive load provided by resistor 106, it is possible to pump and fire the xenon flash 14 at the desired frequency of at least 0.5 hertz.

FIG. 15 illustrates the microcontroller circuit 28, which includes a microcontroller 150, preferably a Motorola 68HC11. However, other microcontrollers or microprocessors using stand alone memory can, of course, alternatively be used. Input signals to the microcontroller 150 includes a ZERO CROSS signal on line 152, which is derived from the AC power, input to the base of the bipolar junction transistor through the resistor illustrated. The ZERO CROSS signal provides a zero cross reference that is used by microcontroller 150 to synchronize the firing of the xenon flash 14 with the AC cycle line frequency. Synchronizing firing of the xenon flash tube with respect to the AC cycle line frequency effectively eliminates 60 hertz cycle noise, as it effects the circuits in exactly the same manner every time flash xenon flash 14 is fired. Also input to the microcontroller 150 are the VCAP signal, as well as the detected reference signal 102 and the detected signal 100. Lines 156 output from microcontroller 150 connect to the display device 32 illustrated in FIG. 1. Similarly, lines 158 are used to attach keyboard 34 to the microcontroller.

Also output from microcontroller 150 is a FAN SPEED signal which controls the speed of a multi speed fan, according to the heat that is generated by xenon flash 14 and the corresponding circuitry. Such heat is assumed as generated by microcontroller 150 when xenon flash 14 is fired. Thus, the multi speed fan may be set to a high speed setting after the initial flash and until some period of time after the last flash occurs.

Operation of the spectrofluorimeter 10, according to the present invention and using the preferred structure above described, will now be further elaborated upon with reference to the flow chart of FIG. 16, which flowchart provides the sequence steps necessary to program the microcontroller 150 with the sequence of program instructions, for each step, that will control operation of the spectroflourimeter as described hereinbefore and hereinafter.

In the initial operation step 200, the user will set spectrofluorimeter 10 to the desired mode of operation, the desired output display mode, as well as the desired sensitivity sensing characteristics.

With respect to the type of operation mode, reference is made to FIG. 17. In order to properly set up the spectrofluorimeter 10, it is required to first test the solution in which the specimen will be placed. Thus, a zero level is obtained. Pressing one of the "insert zero micrograms per milliliter" keys will configure the spectroflourimeter to perform a test on the solution, without the specimen, and use the results for calibrations described hereinafter. The results of this zero level test are then stored in scratch pad memory of the microcontroller 150 illustrated on FIG. 15.

During initial setup of the spectroflourimeter 10 according to the present invention, a second test corresponding to the second operation mode is also necessary. In this test mode, a pure sample of the molecular structure being searched for in the specimen of interest is diluted into the solution and then analyzed. This test is initiated if the "insert 50 ug/ml std" entry key is pressed as illustrated in FIG. 17. When this test is finished, a set of pure calibrations results are thus obtained. The zero and pure calibration results are used to establish a linear relationship between concentration of the molecular structure of interest and the intensity of fluorescent light output detected by detectors 17 and 19.

Once these two initial tests modes are performed, it is then possible to test the specimen of interest to determine the quantity of that molecular structure in a specimen having an unknown quantity of the molecular structure. This third mode is initiated if the "insert unknown" entry key illustrated in FIG. 17 is pressed.

It should be noted that the two initial test modes needed to properly initialize the spectrofluorimeter 10 need only be performed once, until it is desired to reset initial conditions. Controller 150 will store these calibration values in its scratch pad memory and use them during each subsequent analysis of an unknown specimen.

Figure 16A:
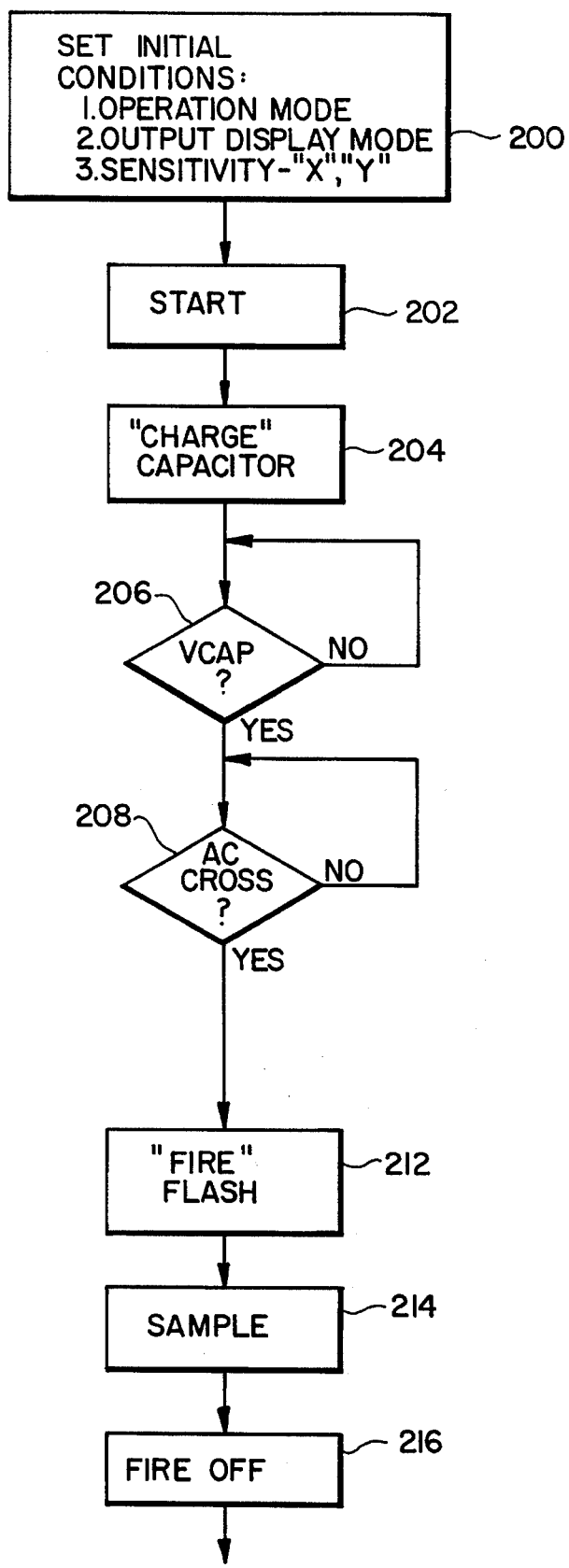
FIG. 16 provides a flow chart outlining the operation of the spectrofluorimeter, controlled with the microcontroller, according to the present invention.
Figure 18:
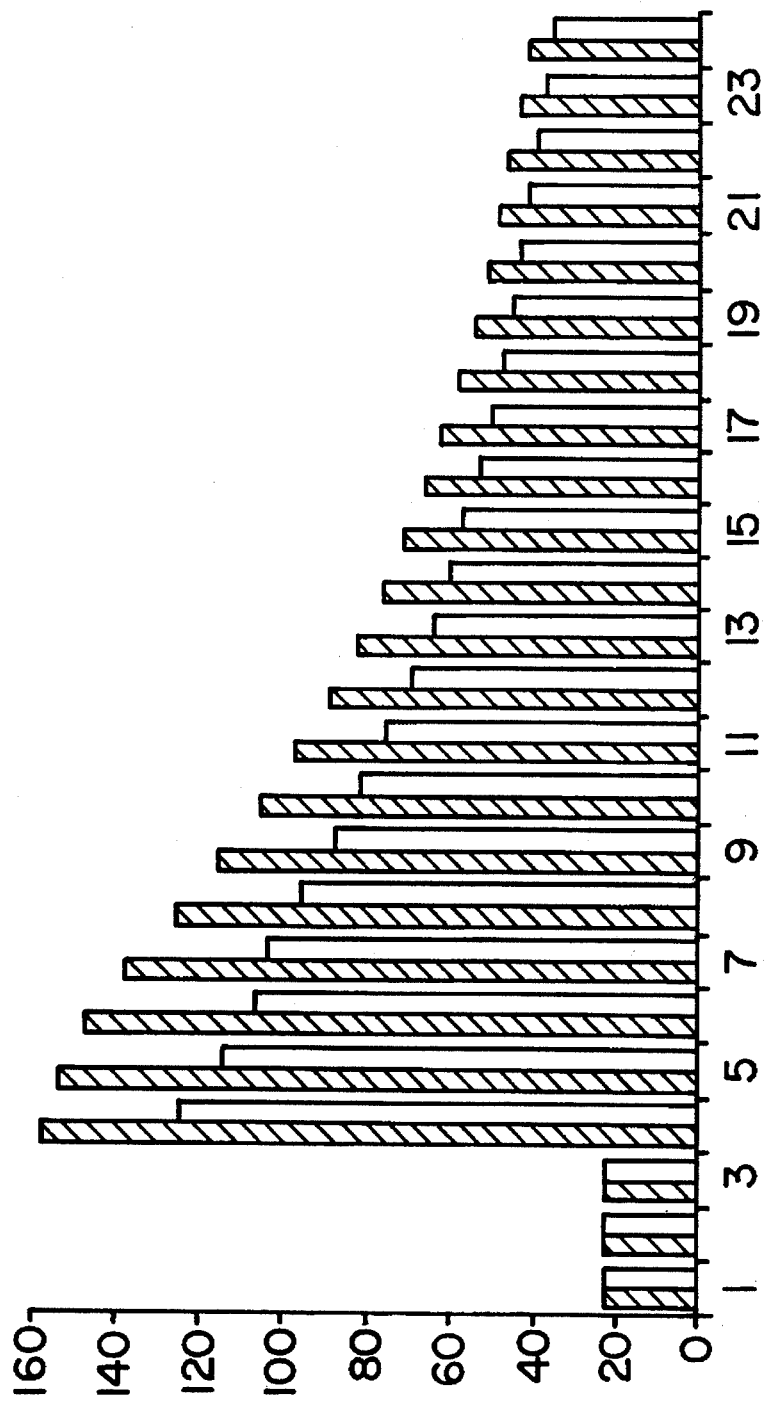
FIG. 18 illustrates samples taken during a single flash cycle when using the spectrofluorimeter according to the present invention.

The second initial condition set by the user in step 200 of FIG. 16 relates to the desired display output type. Reference is again made to FIG. 17. Each of the three vertical columns is representative of the type of output desired. The left column indicates that an output providing the concentration of the molecular structure of interest is desired. The center column indicates that a cell counting mode is desired. The right column indicates that the raw fluorescence value is desired. This value can be used for raw data calculations as desired by the user.

The third initial condition set in the step 200 relates to the sensitivity of the subsequent detections that are to take place. Specifically, because of variances in the intensity of the xenon flash output, it is desirable in certain instances to only use values detected which are obtained when xenon flash pulses of extremely similar intensities are obtained. Thus, the user will set "Y" value, which will be an integer value between 0 and 10 corresponding to permissible drift in the raw florescence VALUE, described hereinafter. This "Y" value represents the permissible drift due to variation in the intensity of the xenon flash, sample turbidity changes and electronic and optical noise. An "X" value will also be set which indicates the number of xenon flash pulses, and thereby detections, the user desires to take place and be averaged together to obtain an average raw florescence value. This raw fluorescence value will then be used in subsequent operations to determine either concentration of the molecular structure or the number cells in this specimen, depending on which output display mode the user selected.

Once these three initial conditions are set, pressing the start key in step 202 initiates operation of the spectroflourimeter. The following steps then occur.

In step 204, the microcontroller 150 of FIG. 15 outputs the CHARGE signal, which signal is used by the capacitor charging circuit 108 illustrated in FIG. 13 to charge the capacitor 104. Step 206 follows, and microcontroller 150 waits for the VCAP signal generated along line 110 to indicate that capacitor 104 is fully charged. Once fully charged, another CHARGE signal is generated by microcontroller 150 in order to change the state of flip flop 142 of FIG. 14, thereby ending the charging of the capacitor 104.

Step 208 follows and microcontroller 150 waits to detect the ZERO CROSS signal which develops on line 152, illustrated in FIG. 15. Once the ZERO CROSS signal is detected by microcontroller 150, microcontroller 150 generates the FIRE signal, which is then output and used to trigger the silicon controlled rectifier 114 illustrated in FIG. 13. This causes triggering of the xenon flash 14 and the initiation of the light pulse. Prior to actual firing of the xenon flash, the FIRE signal, termed DISABLE signal after amplification described previously with reference to FIG. 14, causes connection of each of the detector circuits 16, 18 and 20 illustrated in FIGS. 9, 10 and 11, respectively, to the signal conditioning circuit 26 illustrated in FIG. 12. Connection of these detector circuits allows sampling of the detector values to begin before the flash pulse results, which allows a baseline to be established and used as described hereinafter.

Thus, in step 214 an analog signal representing the amplified, summed and further amplified florescent signal develops along line 800 and a similarly developed analog reference signal develops along line 102. Microcontroller 150 inputs these analog signals to obtain 16 different samples of each signal. It has been determined that a 244 microsecond window with a xenon flash as described previously provides the best results.

Once this 244 microsecond window has elapsed, during which time sampling has taking place, step 216 follows and the microcontroller 15 stops generating the FIRE signal. This effectively disconnects each of the detector circuits 16, 18 and 20 from the signal conditioning circuit 26 illustrated in FIG. 1.

Step 218 then follows in which microcontroller 150 performs a subtraction operation and subtracts the base line data from the signal and reference samples to obtain a normalized sample signal values and normalized reference values. Each of these normalized sample values are then averaged together to obtain a single normalized signal value and a single normalized reference value.

Once these normalized values are determined, step 220 occurs and the last obtained normalized reference value is compared with the previous normalized reference values. If the difference between the last obtained normalized reference value and the previous normalized reference values is greater than the "Y" sensitivity limit described in step 200 previously, then both the normalized reference values and associated normalized signal values are not used in the following addition step 222. In the following step, the total number, which will be an integer, of normalized reference values within the "Y" sensitivity limits is compared to the initial condition "X" value to determine if there exist the required "X" number of normalized values within the predetermined sensitivity limits.

If in step 222 it is determined that enough samples do not exist, microcontroller 150 returns to step 204 and charges the capacitor 104 so that another set of readings can be obtained. Of course, step 204 will need to be repeated, at minimum, at least "X" number of times. It has been determined that X=6, corresponding to six flashes of the xenon flash 14 provides a very effective final normalized value.

If in step 222 the number of normalized values is the same as the X value, each of the normalized signal values are averaged together to obtain a "VALUE" as termed in Table 1 below, in step 224. During step 226, this final VALUE, in some form, is then displayed on display 32, illustrated FIG. 1. Mathematical operations are required to convert the final VALUE to either a concentration of cell count number, depending upon the output characteristics desired. The mathematical operations required to obtain the proper display output are set forth in the following Table 1:

TABLE

FLUORESCENCE raw = Value

CONCENTRATION low = Value for 0 ug/ml
$$high = \frac{Value\ for\ 50\ ug}{ml}$$

$$m = \frac{500}{high - low}$$

b = 0 − m * low
Sample in ng = m * Value + b $$Original = \frac{Sample\ in\ ng}{Sample\ Volume}$$

TABLE-continued

CELL COUNTING low = Value for 0 ug/ml
$$high = \frac{Value\ for\ 50\ ug}{ml}$$

$$m = \frac{500}{high - low}$$

b = 0 − m * low
Sample in ng = m * Value + b
Denatured DNA = Sample in ng * 2

$$Total\ \#\ cells = \frac{Denatured\ DNA * 1000}{pg/dna/cell}$$

Although the present invention is preferably directed to a spectroflourimeter as described above, with certain modifications many of the advantageous characteristics can also be used in a photometer as well. Referring to FIG. 3, a photometer could be implemented using a broad spectrum detector located in place of light absorbing medium 42. This broad spectrum detector would comprise multiple individual detectors, each capable of detecting a different frequency of interest. Each of the detected signals would be amplified and input into microcontroller 150, which would then digitize each sample, and after normalizations and sensitivity comparisons as described above for each wavelength of interest, output and display the value for each detected wavelength of interest. When configured as a photometer, the multiple individual detectors replace detectors 17 and 19 described above with reference to spectroflourimeter 10.

Various arrangements of the detectors within the optical cell cavity are also possible. For instance, reference detector 21 could be placed behind cuvette 40 as illustrated in FIG. 3. Also only one detector of detectors 17 and 19 could be used and the advantageous characteristics of the present invention would still be obtained.

While the invention has been described in connection with what is presently considered to be the most practical and preferred embodiments, it is understood that the invention is not limited to the disclosed embodiment, but, on the contrary, is intended to cover various modifications and equivalent arrangements included within the spirit and scope of the appended claims.

I claim:

1. A detector arrangement for use in a spectrofluorimeter that detects the presence of light emitted from a specimen in solution with a fluorophore comprising:

a light source which produces a pulse of light:
   a detector which detects light emitted from said specimen in solution with said fluorophore, said detector including:
      a first photodiode which produces a first emitted light signal proportional to said emitted light;
   an optical cell made of a light absorbing medium, said optical cell containing, in hollowed out portions of said optical cell, a specimen holding area, a light receiving pathway disposed between said light source and said specimen holding area, and an emitted light pathway disposed between said specimen holding area and said first photodiode; and
   an amplifier which amplifies said first emitted light signal produced by said first photodiode, said amplifier being disposed on a circuit board attached to said optical cell.

2. A detector arrangement for use in a spectrofluorimeter according to claim 1 further comprising:

a reference photodiode which produces a reference light signal proportional to said radiated pulse of light; and wherein said optical cell cavity further comprises a reference light pathway disposed between said light source and said reference photodiode.

3. A detector arrangement for use in a spectrofluorimeter according to claim 2 wherein said optical cell contains a plurality of flat outer surface faces and said circuit board is disposed on a first flat outer surface face, said first flat outer surface face being closest in proximity to said first photodiode.

4. A detector arrangement for use in a spectrofluorimeter according to claim 2 wherein:

said detector includes a second photodiode which produces a second emitted light signal proportional to said emitted light detected by said second photodiode; and said optical cell contains a second emitted light pathway disposed between said specimen holding area and said second photodiode, said emitted light pathway and said second emitted light pathway both substantially at 90° to said light receiving pathway.

5. A detector arrangement for use in a spectrofluorimeter according to claim 4 wherein said amplifier further comprises:

a first amplifier which amplifies said first emitted light signal produced by said first photodiode;

a second amplifier which amplifies said second emitted light signal produced by said second photodiode;

a third amplifier which amplifies said reference light signal produced by said reference photodiode, each of said first, second and third amplifiers being disposed on said circuit board attached to said optical cell.

6. A detector arrangement for use in a spectrofluorimeter according to claim 5 wherein said optical cell contains a plurality of flat outer surface faces and wherein said circuit board is separated into first, second, and third circuit board portions, containing, respectively, said first, second and third amplifiers and wherein said first, second and third circuit board portions are attached to the flat outer surface face being closest in proximity to said photodiode, said second photodiode and said reference photodiode, respectively.

7. A detector arrangement for use in a spectrofluorimeter according to claim 2 wherein said light receiving pathway measures approximately 10 mm and said emitted light pathway measures approximately 10 mm.

8. A detector arrangement for use in a spectrofluorimeter according to claim 7 wherein said light receiving pathway includes a rectangular slit having a width of approximately 3 mm and a height of approximately 7 mm.

9. A detector arrangement for use in a spectrofluorimeter according to claim 7 wherein said reference light pathway measures greater than 10 mm.

10. A detector arrangement according to claim 1 wherein a further hollow portion of said optical cell is located along said emitted light pathway behind said specimen holding area.

11. A detector arrangement according to claim 10 wherein a light absorbing material is disposed behind said further hollow portion along said emitted light path behind said specimen holding area.

12. A detector arrangement according to claim 2 wherein each of said first photodiode and said reference photodiode is held in a light tight configuration within said hollowed portions of said optical cell using an o-ring.

13. A detector arrangement according to claim 1 wherein said pulse of light is approximately a 600 nm pulse of approximately 30,000 watts.

14. A spectrofluorimeter for detecting the presence of light emitted from a specimen in solution with a fluorophore comprising:

a triggered light source;

a capacitor capable of being charged with electrical energy and subsequently discharging said electrical energy;

a detector which detects emitted light from said specimen, said detector producing an emitted light signal proportional to said emitted light; and a computer which uses a sequence of program instructions to cause:

a charging and discharging of said capacitor by generating a charge signal to cause charging of said capacitor and generating a fire signal to cause discharging of said capacitor and thereby triggering said light source;

inputting to said computer a baseline signal obtained from said detector prior to triggering said light source; and inputting to said computer said emitted light signal obtained from said detector.

15. A spectrofluorimeter according to claim 14 further comprising a reference detector which produces a reference light signal proportional to said pulse of light so that said emitted light signal which is input into said computer is normalized using said baseline signal and said reference light signal.

16. A spectrofluorimeter according to claim 15 wherein:

said computer initiates said charge and fire signals successively a plurality of times, thereby obtaining a plurality of baseline signals and reference light signals and causing a plurality of pulses of light which result in a plurality of light emission signals, each of said plurality of light emission signals being input into computer and normalized by said computer using said baseline signals and said reference light signals.

17. A spectrofluorimeter according to claim 16 wherein said computer causes said plurality of normalized light emission signals to be compared with a sensitivity limit range so that those normalized light emission signals having a value below said sensitivity limit range are not subsequently used to determine a quantity of said specimen in said solution.

18. A spectrofluorimeter according to claim 17 wherein a minimum number of said normalized light emission signals must be obtained before said computer determines said quantity of said specimen in said solution.

19. A spectrofluorimeter according to claim 18 wherein said minimum number is 6.

20. A spectrofluorimeter according to claim 17 further comprising an AC cycle line zero crossing reference detector which generates a zero cross signal used by said computer means in determining when to trigger said light source.

21. A detector arrangement for use in a spectrofluorimeter that detects the presence of light emitted from a specimen in solution with a fluorophore comprising:

a light source which produces a pulse of light:

first and second specimen detectors which detect light emitted from said specimen in solution with said fluorophore and produce first and second emitted light signals proportional to said emitted light;

a reference detector which produces a reference light signal proportional to said radiated pulse of light;

an optical cell made of a light absorbing medium, said optical cell containing a specimen holding area, a light receiving pathway disposed between said light source and said specimen holding area, emitted light pathways disposed between said specimen holding area, each of said first and second specimen detectors and a reference light pathway disposed between said light source and said reference detector; and an amplifier which amplifies said first and second emitted light signals and said reference light signal.

22. A detector arrangement for use in a spectrofluorimeter according to claim 21 wherein each of said first and second specimen detectors can be electrically coupled to first and second amplifiers respectively and said reference detector can be electrically coupled to a third amplifier, each of said first, second, and third amplifiers being disposed on a circuit board attached to said optical cell.

23. A detector arrangement for use in a spectrofluorimeter according to claim 22 wherein said optical cell contains a plurality of flat outer surface faces and wherein said circuit board is separated into first, second, and third circuit board portions, containing, respectively, said first, second and third amplifiers and wherein said first, second and third circuit board portions are attached to the flat outer surface face being closest in proximity to said first and second specimen detectors and said reference detector, respectively.

24. A detector arrangement for use in a spectrofluorimeter according to claim 22 further including a summer which sums the amplified first and second emitted light signals output from said first and second amplifiers to obtain a summed output signal; and a summing amplifier for amplifying said summed output signal.

25. A spectrofluorimeter for detecting the presence of light emitted from a specimen in solution with a fluorophore comprising:

a triggered light source which produces pulses of light;

a capacitor capable of being charged with electrical energy and subsequently discharging said electrical energy;

a detector which detects emitted light from said specimen, said detector producing an emitted light signal proportional to said emitted light;

an AC cycle line zero crossing reference detector which generates a zero cross signal; and a computer which uses a sequence of program instructions to cause:

charging and discharging of said capacitor by generating a charge signal to cause charging of said capacitor and generating a fire signal after inputting said zero cross signal to cause discharging of said capacitor and thereby triggering said light source, and inputting to said computer said emitted light signal obtained from said detector.

26. A spectrofluorimeter according to claim 25 wherein said computer controls with said sequence of program instructions inputting of a baseline signal obtained from said detector prior to triggering said light source.

27. A spectrofluorimeter according to claim 26 further comprising a reference detector which produces a reference light signal proportional to said pulse of light so that said emitted light signal which is input into said computer is normalized using said baseline signal and said reference light signal.

28. A spectrofluorimeter according to claim 27 wherein:

said computer initiates said charge and fire signals a plurality of times, thereby obtaining a plurality of baseline signals and reference light signals and causing a plurality of pulses of light which result in a plurality of light emission signals, each of said plurality of light emission signals being input into said computer and normalized by said computer using said baseline signals and said reference light signals, and wherein said computer compares said plurality of normalized light emission signals with a sensitivity limit range so that those normalized light emission signals having a value below said sensitivity limit range are not subsequently used to determine a quantity of said specimen in said solution.

29. A spectrofluorimeter for detecting the presence of light emitted from a specimen in solution with a fluorophore comprising:

a triggered light source which produces pulses of light;

capacitor capable of being charged with electrical energy and subsequently discharging said electrical energy;

a detector which detects emitted light from said specimen, said detector producing a plurality of emitted light signals proportional to said emitted light; and a computer which uses a sequence of program instructions to cause:

charging and discharging of said capacitor by generating a plurality of charge signals to cause charging of said capacitor and generating a plurality of fire signals to cause discharging of said capacitor and thereby triggering said light source a plurality of times and thereby obtaining said plurality of emitted light signals, inputting to said computer said plurality of emitted light signals obtained from said detector, comparing said plurality of emitted light signals with a sensitivity limit range so that those emitted light signals having a value below said sensitivity limit range are not subsequently used to determine a quantity of said specimen in said solution.

30. A spectrofluorimeter according to claim 29 wherein a minimum number of said emitted light signals must be obtained before said computer determines said quantity of said specimen in said solution.

* * * * *